(12) United States Patent
Gradel

(10) Patent No.: US 10,702,287 B2
(45) Date of Patent: Jul. 7, 2020

(54) METHOD FOR PRODUCING A REAMER

(71) Applicant: Deuxventorio Sàrl, Gland (CH)

(72) Inventor: Thomas Gradel, Marignier (FR)

(73) Assignee: DEUXVENTORIO SÀRL, Gland (CH)

( * ) Notice: Subject to any disclaimer, the term of this patent is extended or adjusted under 35 U.S.C. 154(b) by 226 days.

(21) Appl. No.: 15/523,707

(22) PCT Filed: Nov. 6, 2015

(86) PCT No.: PCT/IB2015/058569
§ 371 (c)(1),
(2) Date: May 2, 2017

(87) PCT Pub. No.: WO2016/071867
PCT Pub. Date: Mar. 12, 2016

(65) Prior Publication Data
US 2017/0311958 A1  Nov. 2, 2017

(30) Foreign Application Priority Data

Nov. 7, 2014 (FR) ..................... 14 60811

(51) Int. Cl.
*A61B 17/16* (2006.01)
*B21D 35/00* (2006.01)
*A61B 17/00* (2006.01)

(52) U.S. Cl.
CPC ........ *A61B 17/1666* (2013.01); *B21D 35/001* (2013.01); *A61B 2017/00526* (2013.01); *A61B 2017/1602* (2013.01)

(58) Field of Classification Search
CPC ........ A61B 17/1666; A61B 2017/1602; A61B 2017/0052; A61B 17/1617; A61B 17/162; A61B 2017/0046; A61B 2017/007477; A61B 17/1615; A61B 17/1659; B21D 35/001; Y10T 26/49995; A61F 2/4684
USPC .................. 76/115; 29/557; 606/81
See application file for complete search history.

(56) References Cited

U.S. PATENT DOCUMENTS

| | | | | |
|---|---|---|---|---|
| 4,037,494 A | * | 7/1977 | Hess | ..................... B02C 18/362 76/115 |
| 5,976,148 A | * | 11/1999 | Charpenet | ................. A61F 2/34 606/100 |
| 6,168,600 B1 | * | 1/2001 | Grace | ................ A61B 17/1666 606/81 |
| 6,520,888 B1 | * | 2/2003 | Itoh | ......................... F16H 15/38 384/623 |
| 2005/0061407 A1 | * | 3/2005 | Ono | ....................... B21D 13/02 148/645 |

(Continued)

FOREIGN PATENT DOCUMENTS

EP  0704191 A1  4/1996
EP  1129667 A1  9/2001

(Continued)

*Primary Examiner* — Ghassem Alie
(74) *Attorney, Agent, or Firm* — William H. Eilberg

(57) ABSTRACT

Method for producing a reamer such as a milling cutter intended to mill the acetabular cavity of a patient, the reamer including a rigid base with an interface for coupling to a tool holder, and including a cutter body which has a thin wall and is perforated and toothed. The rigid base is produced separately from the cutter body, by cutting out and drawing a first flat metal blank in a press.

9 Claims, 5 Drawing Sheets

(56) References Cited

U.S. PATENT DOCUMENTS

| | | | |
|---|---|---|---|
| 2009/0163921 A1 | 6/2009 | Lechot | |
| 2010/0069908 A1* | 3/2010 | Sidebotham | A61B 17/1617 606/81 |
| 2012/0191099 A1* | 7/2012 | Victor | A61B 17/1666 606/81 |
| 2013/0245628 A1* | 9/2013 | Sidebotham | A61B 17/16 606/80 |

FOREIGN PATENT DOCUMENTS

| | | |
|---|---|---|
| EP | 1624814 B1 | 10/2007 |
| EP | 2359755 A1 | 8/2011 |
| EP | 2478852 A1 | 7/2012 |

* cited by examiner

METHOD FOR PRODUCING A REAMER

TECHNICAL FIELD OF THE INVENTION

The present invention relates to a method for producing a reamer, such as a milling cutter intended to mill the acetabular cavity of a patient during hip surgery.

A known example of a reamer is described in the document EP 2 359 755. This reamer comprises an at least partially circular rigid base with a substantially cylindrical lateral surface having a coupling interface for coupling to a tool holder and having radial receiving lugs for receiving a cutter body. A thin-walled, perforated and toothed cutter body is attached and fixed to the rigid base, the cutter body having engagement interfaces for engaging with the radial receiving lugs of the rigid base.

The rigid base is complex to produce, particularly for the realization of the coupling interface and of the radial receiving lugs. This complexity means that the cost of producing the reamer is very high.

Now, in order to guarantee perfect sterility of the operating theater and to limit as far as possible the risk of infection of the patient, increasing numbers of practitioners wish to have a disposable tool holder that is supplied in the sterile state to the operating theater and that is disposed of after use. This requires the provision of an inexpensive reamer, which is impossible in the case of the reamer from the document EP 2 359 755 on account of the complexity of the rigid base.

The document US 2009/0163921 describes a method for producing a reamer, during which method a cutter body is produced by cutting out and stamping. The rigid base has a shape that it is not possible to obtain by a simple, quick and inexpensive method. The document US 2009/0163921 teaches more particularly the production of the rigid base by a molding method.

DISCLOSURE OF THE INVENTION

The problem addressed by the invention is that of developing a production method permitting rapid and less expensive production of a reamer, such as a milling cutter intended to mill the acetabular cavity of a patient, comprising a rigid base with a coupling interface for coupling to a tool holder, and comprising a thin-walled, perforated and toothed cutter body.

To achieve these aims and others, the invention proposes a method for producing a reamer such as a milling cutter intended to mill the acetabular cavity of a patient, said reamer comprising a rigid base with a coupling interface for coupling to a tool holder, and comprising a cutter body with a thin, perforated and toothed wall;
according to the invention, the rigid base is produced separately from the cutter body, by cutting out and press-stamping of a first flat metal panel.

A production method of this kind is quick, easy to carry out and sufficiently inexpensive so that the reamer has a sufficiently low production cost and the users are subsequently able to use it just once.

Advantageously, during the stamping operation, the first panel can be deformed in such a way as to give branches of the coupling interface a U-shaped or V-shaped cross section. This results in a branched coupling interface having satisfactory rigidity, despite having been obtained from cutting out a flat panel.

Preferably, the cutter body can be produced separately from the rigid base, by cutting out and press-stamping of a second flat metal panel in order to cut out the cutter body along its contour, perforate the cutter body and form the teeth of the cutter body.

It is thus possible, in a simple, quick and cost-effective manner, to form the teeth on the second panel while held flat, since it is not yet shaped into a hemisphere, which is easier to do than when the cutter body is already connected to the rigid base and thus shaped into a hemisphere.

Advantageously, the method can comprise the following steps:
a) supplying a rigid base,
b) supplying a cutter body blank formed by a second flat panel having a plurality of perforated and toothed petals which extend radially from a central zone, to which they are connected, as far as a free end with an end edge, and which are separated from one another by radial lateral spaces,
c) shaping the cutter body into a hemisphere,
d) attaching the rigid base to the hemispherical cutter body.

A production method of this kind is easy and quick to carry out and can also be automated. After said second panel (which can have a constant thickness) has been cut out and stamped, it is shaped into a hemisphere by bringing the free ends of the petals closer together, in order then to be fixed to the rigid base. This bringing closer together is permitted by the radial lateral spaces situated between the petals, which spaces tend to grow smaller during the bringing together. The cutter body is finally in the form of a panel (optionally of constant thickness) having a plurality of inwardly curved petals extending radially from the central zone as far their free end with the end edge.

Advantageously, provision can be made that:
the rigid base is at least partially circular with a substantially cylindrical lateral surface having a coupling interface for coupling to a tool holder, and having radial receiving lugs for receiving the cutter body,
the perforated and toothed cutter body with the thin wall has engagement interfaces for engaging with the radial receiving lugs of the rigid base,
the coupling interface and the radial receiving lugs have lateral facets parallel to a cylinder axis of the substantially cylindrical lateral surface of the rigid base,
during step d), all the radial receiving lugs are caused to enter the respective engagement interfaces by a simple combined movement of translation.

The particular shape of the coupling interface and of the radial receiving lugs is compatible with production of the rigid base by a method of cutting and press-stamping starting from a flat metal panel. Moreover, the movement of translation for assembling the cutter body and the rigid base is simple to effect with the aid of a robot.

Preferably, the free end of each petal can have at least one engagement interface having a notch which is formed in the end edge of the petal and in which one of the radial receiving lugs of the rigid base engages. The notches mean that the panel shaped into a hemisphere can be positioned correctly with respect to the rigid base before being definitively joined to the rigid base. This effectively limits the risks of the cutter body of the reamer, after assembly to the rigid base, having an incorrect geometry, that is to say deviating from the general shape of a hemisphere. Being formed in the end edge of the petals, the notches are able to receive the radial receiving lugs of the rigid base in a simple movement of translation after the cutter body has been completely shaped into a hemisphere.

Advantageously, provision can be made that:
each petal has two lateral edges extending radially from the central zone as far as the end edge,
each petal has an engagement interface having two substantially L-shaped notches, respectively, formed between the end edge and one of the lateral edges.

The L-shaped notches of two adjacent petals thus form, by interaction, substantially U-shaped notches that are able to receive the radial receiving lugs of the rigid base. The radial receiving lugs thus define a predetermined satisfactory distance between two adjacent petals. Moreover, the free ends of the petals can thus be fixed to the rigid base at least at two outermost points of their end edge, which limits the risks of deformation of the petals by warping during the operations of milling the acetabular cavity of the patient. It is likewise possible for the free ends of the petals to be fixed to the rigid base along the entire length of their end edge.

Preferably, during a step e), the free end of the petals can be fixed by welding or by adhesive bonding to the substantially cylindrical lateral surface of the rigid base. Such fixing can be done quickly and easily, especially by robot.

Preferably, provision can be made that:
the rigid base is at least partially circular with a substantially cylindrical lateral surface,
the coupling interface has at least two branches which extend from the center of the rigid base and which are connected to the substantially cylindrical lateral surface.

These branches will be able to be received in tool holders with a mounting plate of the bayonet type having notches with a substantially L-shaped longitudinal profile, which are illustrated in the documents EP 0 704 191, EP 1 129 667 and EP 1 624 814 and which are already found in operating theaters in most hospitals. Therefore, practitioners do not require the purchase of a specific tool holder in order to use the reamer according to the invention.

The reamer may nevertheless comprise a different number of branches on its rigid base, for example three or four, or even more.

Advantageously, the coupling interface can be in the form of a cross, of which at least two branches extend from the center of the rigid base and are connected to the substantially cylindrical lateral surface. The two branches that do not extend as far as the rigid base make it possible to hold the reamer fixed in orientation around the axial directions that are defined by the two other branches. This hold is obtained by interaction with the mounting plate of the tool holder, in most cases by simple pressure against the mounting plate of the tool holder.

BRIEF DESCRIPTION OF THE DRAWINGS

Other subjects, features and advantages of the present invention will become clear from the following description of particular embodiments, with reference being made to the attached figures, in which.

DESCRIPTION OF PREFERRED EMBODIMENTS

Figure 1:
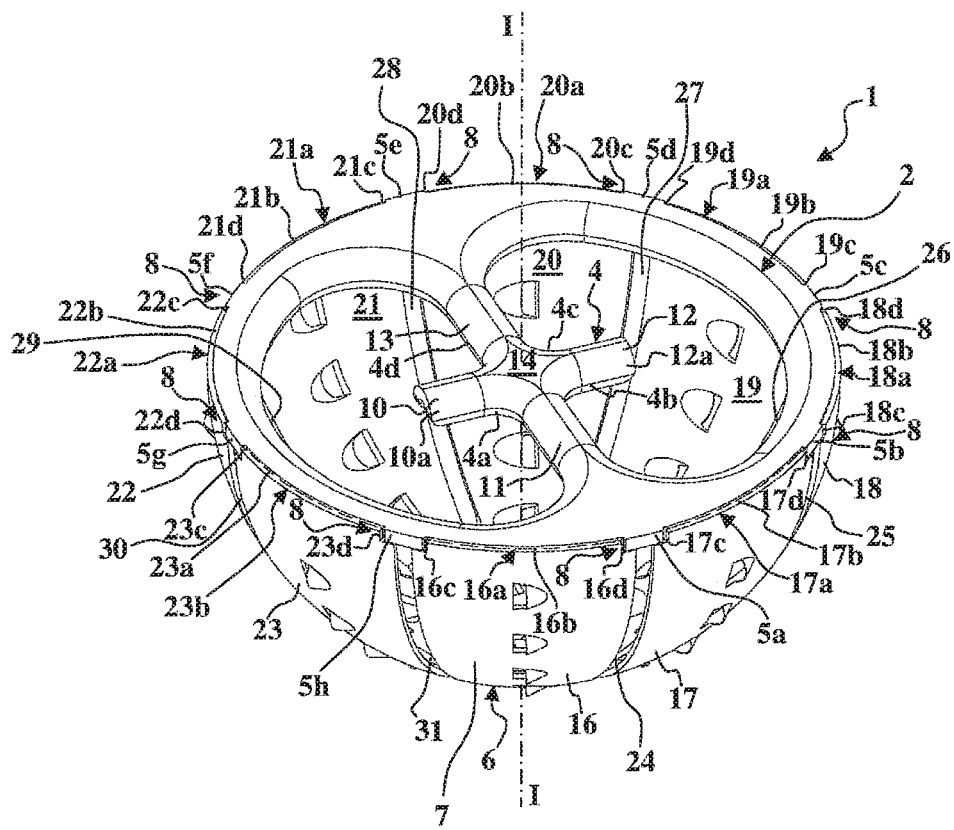
FIG. 1 is a perspective view of an embodiment of a reamer, of which at least the rigid base is obtained by a production method according to the invention.
Figure 2:
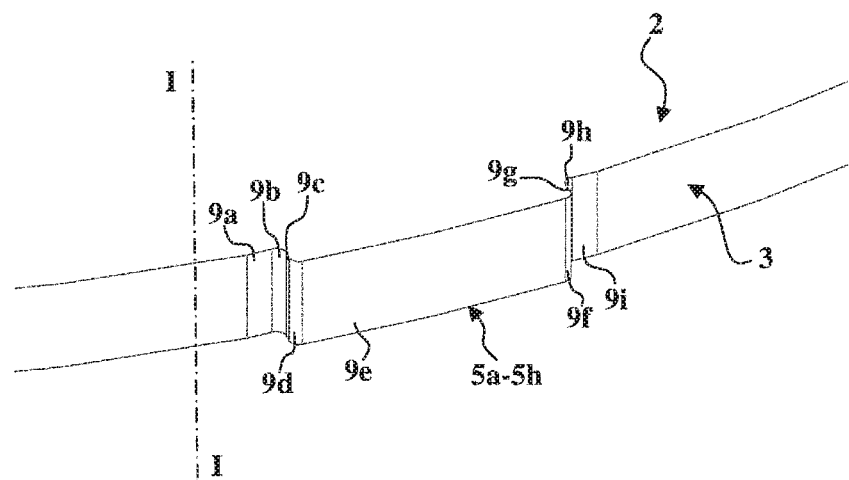
FIG. 2 is a partial perspective view of a detail of the rigid base of the reamer from FIG. 1.
Figure 3:
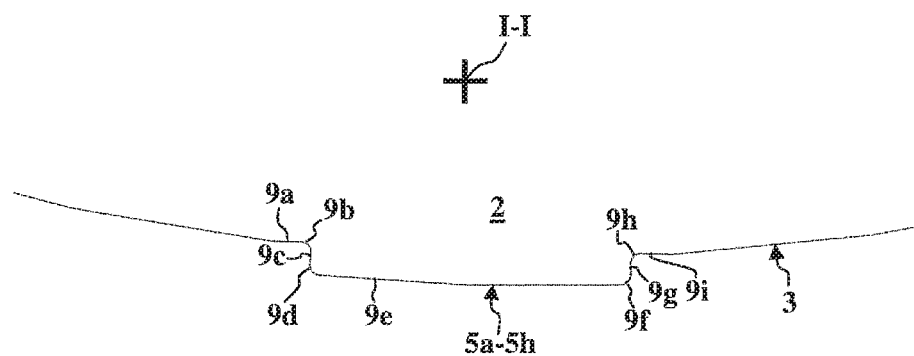
FIG. 3 is a plan view of FIG. 2.

An example of a reamer 1 according to the invention, such as a surgical milling cutter intended to mill the acetabular cavity of a patient, is illustrated in FIGS. 1 to 7.

This reamer comprises:
an at least partially circular rigid base 2 with a substantially cylindrical lateral surface 3 having a coupling interface 4 for coupling to a tool holder, and having radial receiving lugs 5a to 5h for receiving a cutter body 6,
a perforated and toothed cutter body 6 with a thin wall 7, having engagement interfaces 8 for engaging with the radial receiving lugs 5a to 5h of the rigid base 2.

The substantially cylindrical lateral surface 3 extends along a cylinder axis I-I.

Figure 4:
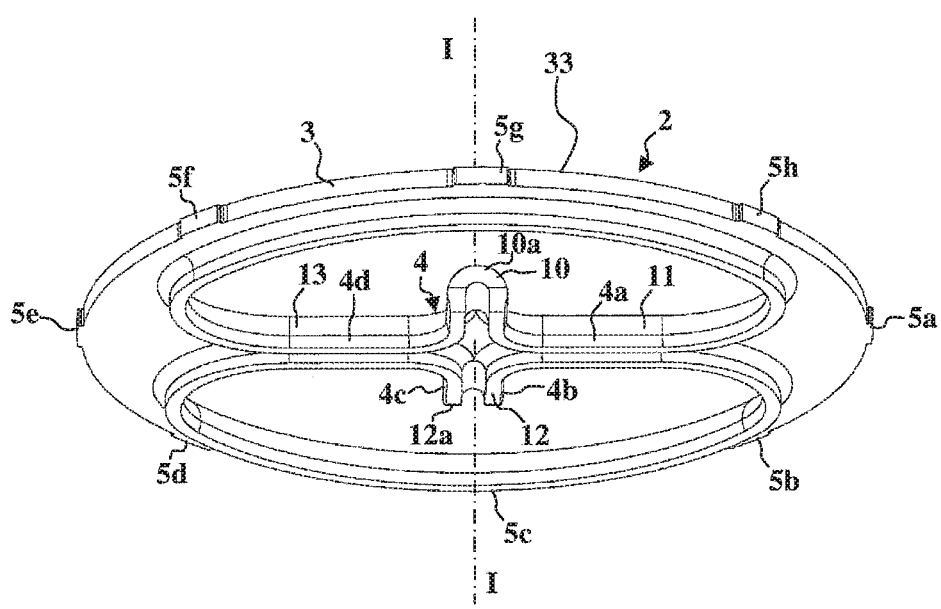
FIG. 4 is a perspective bottom view of the rigid base of the reamer from FIG. 1.
Figure 5:
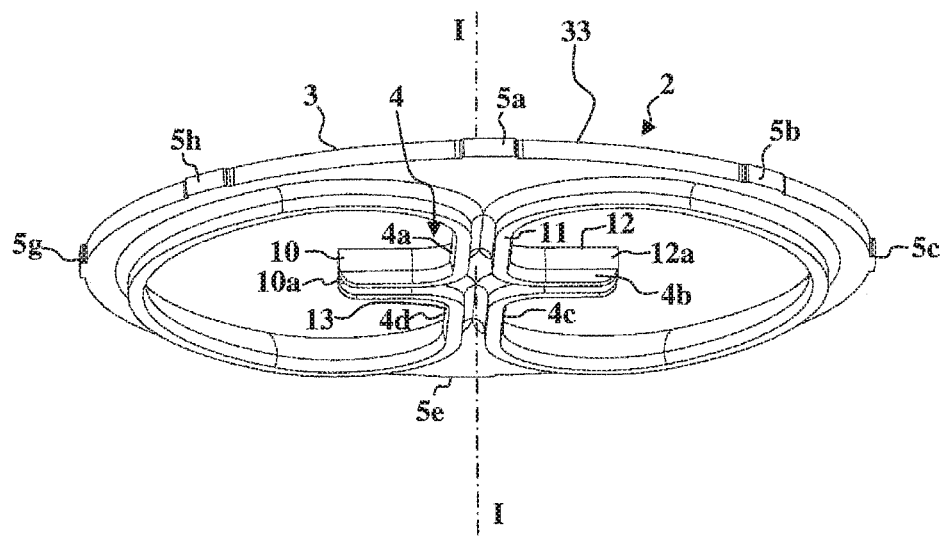
FIG. 5 is another perspective bottom view of the rigid base of the reamer from FIG. 1, in an orientation at 90° with respect to the view in FIG. 4.

It will be seen more particularly in FIGS. 1, 4 and 5 that the coupling interface 4 has lateral facets 4a to 4d which are parallel to the cylinder axis I-I of the substantially cylindrical lateral surface 3 of the rigid base 2. Production of the coupling interface 4, with lateral facets 4a to 4d oriented in this way, is possible by a method of cutting out and press-stamping.

Similarly, the radial receiving lugs 5a to 5h have lateral facets 9a to 9i which are parallel to the cylinder axis I-I of the substantially cylindrical lateral surface 3 of the rigid base 2. The radial receiving lugs 5a to 5h with lateral facets 9a to 9i oriented in this way can also be produced by a method of cutting out and press-stamping, such that the entire rigid base 2 in itself can be obtained by a method of cutting out and press-stamping of a first flat metal panel 33.

The method of cutting out and press-stamping can be carried out with the aid of a mechanical cutting/stamping press provided with progressive tooling (monitoring tool and/or transfer tools).

The coupling interface 4 has four branches 10 to 13 extending from the center 14 of the rigid base 2. The two branches 11 and 13 are connected to the substantially cylindrical lateral surface 3. The two branches 10 and 12 end in free ends 10a and 12a. However, the branches 10 and 12 can continue as far as the substantially cylindrical lateral surface 3, like the branches 11 and 13.

The coupling interface 4 thus takes the form of a cross, of which at least two branches 11 and 13 extend from the center 14 of the rigid base 2 and are connected to the substantially cylindrical lateral surface 3.

It will be seen more particularly in FIGS. 4 and 5 that the branches 10 to 13 have a substantially U-shaped cross section. A configuration more akin to a V shape is also possible. The open side of the U is oriented in the direction of the interior of the cutter body 6 when the reamer 1 is assembled (FIG. 1). This U-shaped configuration of the branches 10 to 13 can also be obtained, during the same method of cutting out and press-stamping, from the first flat metal panel 33 and gives the branches 10 to 13 good rigidity in order to transmit the torque that will be communicated by the tool holder attached to the branches 10 to 13, in a manner similar to what is illustrated in the documents EP 0 704 191, EP 1 129 667 and EP 1 624 814.

Figure 6:
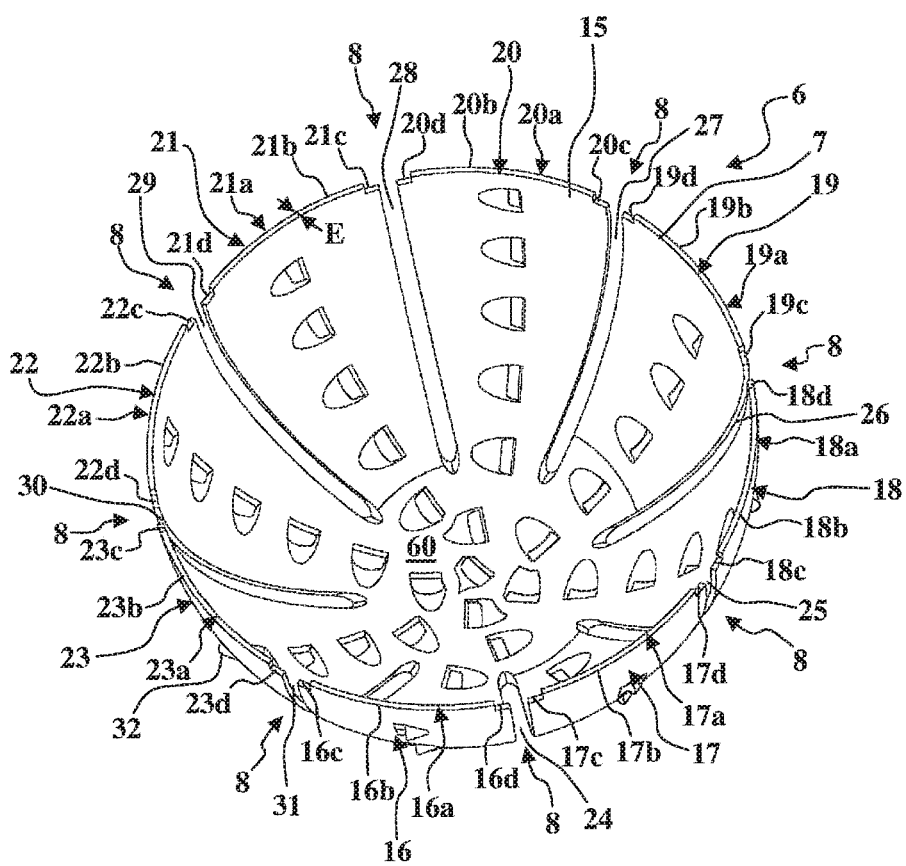
FIG. 6 is a perspective view of the cutter body of the reamer from FIG. 1.
Figure 7:
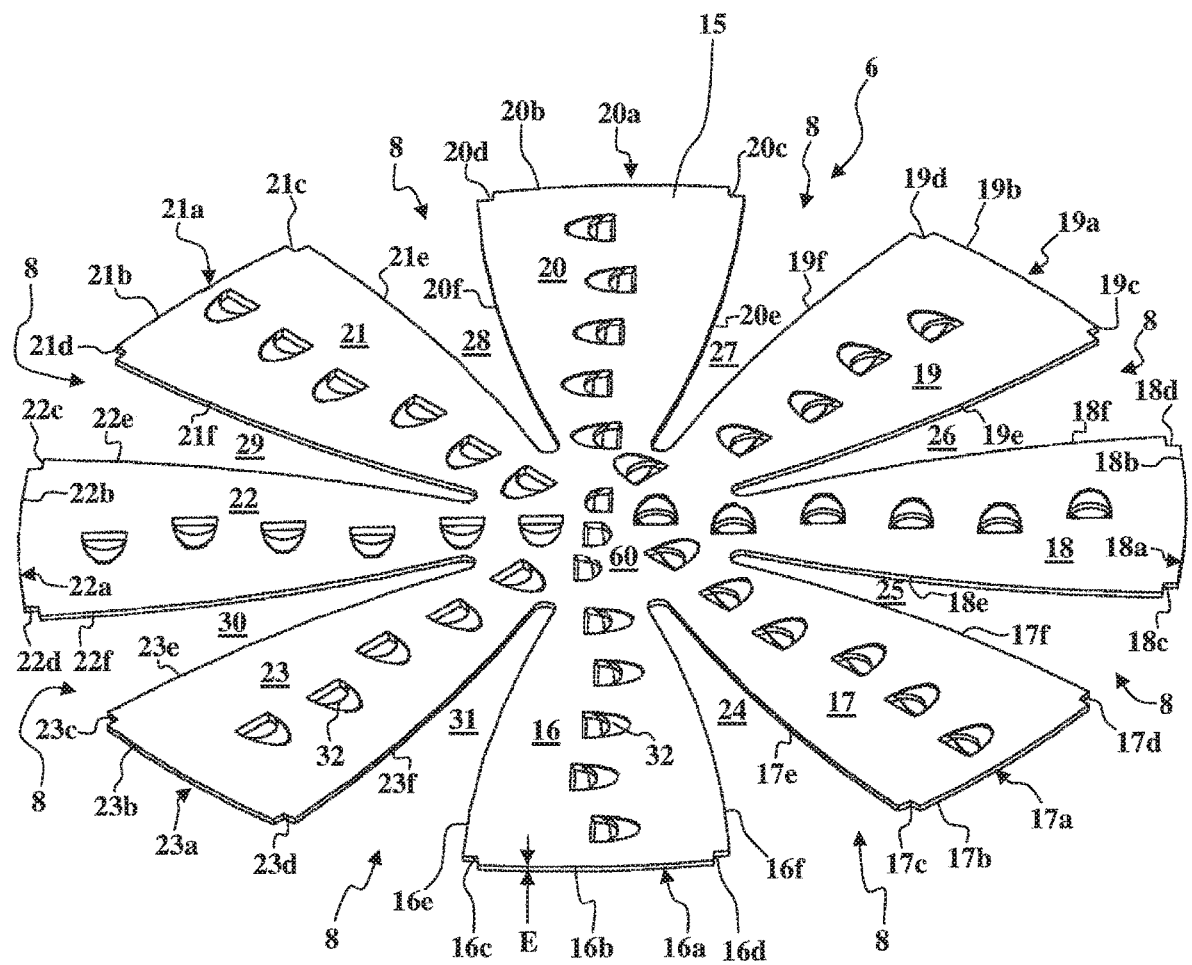
FIG. 7 is a perspective view of the cutter body of the reamer from FIG. 1, before it is shaped into a hemisphere.

It will be seen more particularly in FIGS. 6 and 7 that the cutter body 6 is formed by a second panel 15 of constant thickness E having a plurality of petals 16 to 23 which extend radially from a central zone 60 to a free end 16a to 23a with an end edge 16b to 23b and which are separated from one another by radial lateral spaces 24 to 31.

In FIG. 7, the second panel 15 is illustrated just after its production, carried out separately from the production of the rigid base 2, by a method of cutting out and press-stamping in order to cut out the cutter body 6, perforate the cutter body 6 and form the teeth 32 of the cutter body 6. The method of cutting out and press-stamping can also be carried out with the aid of a mechanical cutting/stamping press provided with progressive tooling (monitoring tools and/or transfer tools).

In FIG. 6, the second panel 15 of the cutter body 6 is illustrated just after it has been shaped into a hemisphere. This configuration is obtained prior to the attachment of the cutter body 6 to the rigid base 2.

It will be seen more particularly in FIG. 7 that each petal 16 to 23 has at least one engagement interface 8 having two L-shaped notches 16c to 23c and 16d to 23d formed in the end edge 16b to 23b and the lateral edges 16e to 23e and 16f to 23f of the petals 16 to 23.

The L-shaped notches 16c to 23c and 16d to 23d form, in pairs, substantially U-shaped notches in which the radial receiving lugs 5a to 5h of the rigid base 2 are received.

After the second panel 15 has been shaped into a hemisphere, the notches are thus oriented in such a way as to receive the radial receiving lugs 5a to 5h in a simple movement of translation in the direction defined by the cylinder axis I-I of the substantially cylindrical lateral surface 3 of the rigid base 2.

Alternatively, substantially U-shaped notches can be formed substantially at the center of the end edges 16b to 23b.

Figure 8:
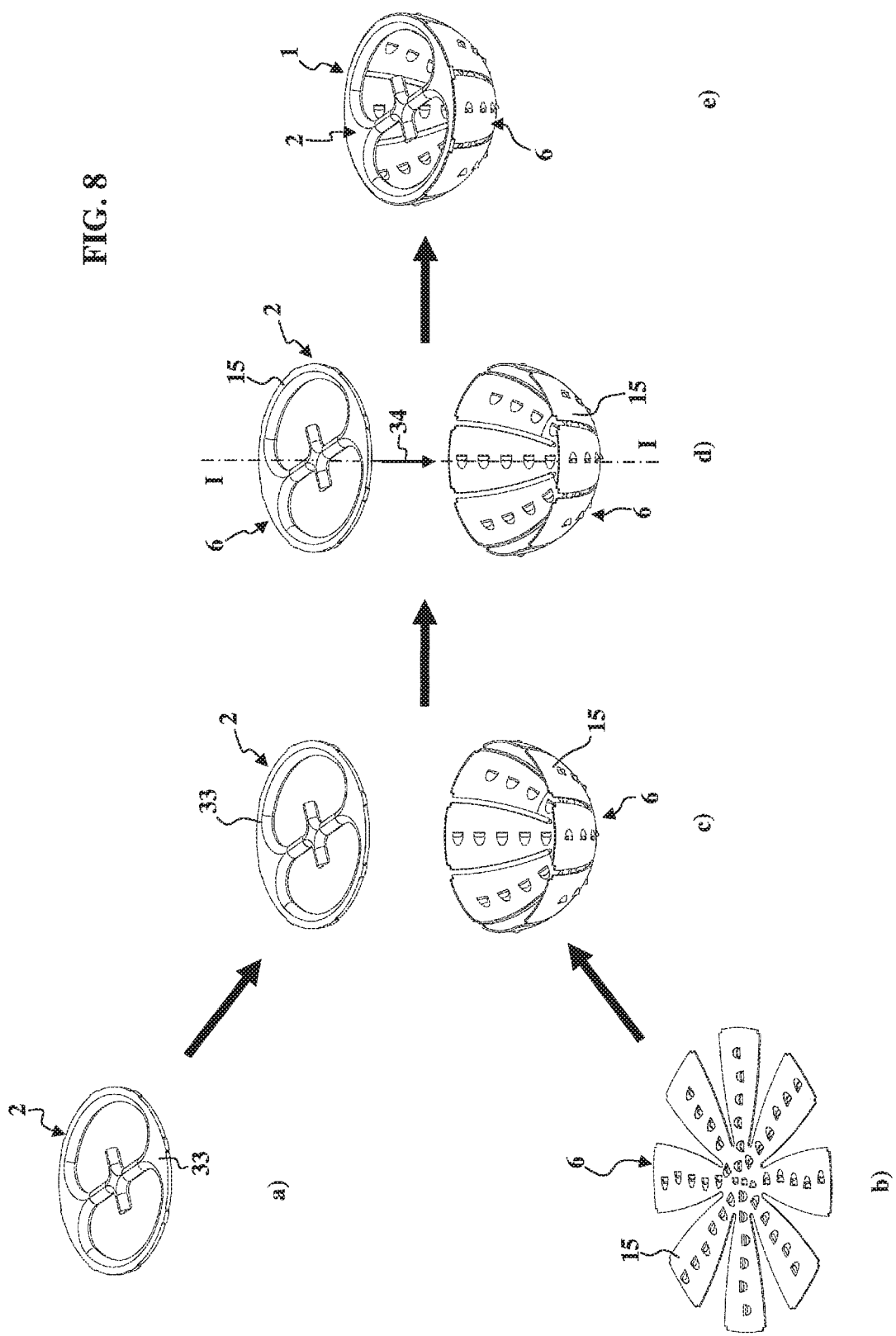
FIG. 8 is a schematic and perspective view illustrating a method for producing the reamer from FIG. 1.

The method of producing the reamer 1 will now be explained, in particular with reference to FIG. 8.

During a step a), a rigid base 2 is made available (the rigid base 2 is identical to that of FIGS. 4 and 5). This rigid base 2 is obtained by cutting out and press-stamping of a first panel 33.

During a step b), a cutter body blank 6 is made available which is formed by a second flat panel 15 having a plurality of perforated and toothed petals 16 to 23 extending radially from a central zone 60, to which they are connected, as far as a free end 16a to 23a with an end edge 16b to 23b. The petals 16 to 23 are separated from one another by radial lateral spaces 24 to 31. The second panel 15 is presented flat. The cutting out of the cutter body blank 6 along its periphery, the perforation of the petals 16 to 23 and the formation of the teeth 32 are carried out by cutting out and press-stamping. The cutter body 6 is thus obtained "flat", as is illustrated in FIG. 7.

During a step c), the cutter body 6 is shaped into a hemisphere, for example by pushing the second panel 15 into a hollow hemispherical mold, for example by means of a hemispherically shaped pusher complementing the hemispherical hollow mold. The cutter body 6 is thus obtained "shaped", as is illustrated in FIG. 6.

During a step d), the rigid base 2 is attached to the hemispherical cutter body 6 by pushing the radial receiving lugs 5a to 5h into the engagement interfaces 8. On account of the orientation of the notches 16c to 23c and 16d to 23d, the radial receiving lugs 5a to 5h engage in the engagement interfaces 8 by a simple movement of translation along the cylinder axis I-I, illustrated by the arrow 34.

Then, during a step e), the free ends 16a to 23a of the petals 16 to 23 are fixed to the substantially cylindrical lateral surface 3 of the rigid base 2 by welding or by adhesive bonding. The reamer illustrated in FIG. 1 is thus obtained.

This fixing can be done via adhesively bonded or welded points formed discretely in the area of the L-shaped notches 16c to 23c and 16d to 23d, that is to say at the two outermost points of the end edges 16b to 23b of the petals 16 to 23. This limits the risks of deformation of the petals 16 to 23 by torsion during the subsequent operations of milling the acetabular cavity of the patient. Fixing the free ends 16a to 23a of the petals 16 to 23 to the rigid base 2 all the way along their end edge 16b to 23b is also possible by means of a continuous string of adhesive or continuous weld.

The present invention is not limited to the embodiments that have been explicitly described, and instead it encompasses the various variants and generalizations contained within the scope of the appended claims.

The invention claimed is:

1. A method for producing a reamer for milling an acetabular cavity of a patient, comprising the steps of:
    a) forming a base by cutting out and press-stamping a first flat piece of metal, the base being generally disk-shaped and having a generally uniform thickness, the base being perforated so as to define a plurality of branches extending from a center of the base, wherein the press-stamping step includes the step of deforming the first flat piece of metal so that the branches have a U-shaped or V-shaped cross-section,
    b) forming a cutter body by providing a blank made by cutting out and press-stamping a second flat piece of metal which is separate from the first flat piece of metal,
    c) shaping the cutter body into a hemisphere, and
    d) attaching the base to the hemispherical cutter body.

2. The method of claim 1, wherein step (b) further comprises forming the second flat piece of metal into a plurality of perforated and toothed petals which extend radially from a central zone, to which they are connected, as far as a free end with an end edge, and which are separated from one another by radial lateral spaces.

3. The method of claim 2, wherein the U-shaped or V-shaped cross-section of the branches are produced by deformation during the press-stamping process of step (a).

4. The method of claim 3, wherein the cutting out and press-stamping of step (b) includes cutting the cutter body along a cutting body contour, and perforating the cutter body to form teeth in the cutter body.

5. The method of claim 4, wherein:
    the base has a substantially cylindrical lateral surface having a coupling interface for coupling to a tool holder, the base also having radial receiving lugs for receiving the cutter body,
    the cutter body has engagement interfaces for engaging with the radial receiving lugs of the base,
    the coupling interface and the radial receiving lugs have lateral facets parallel to a cylinder axis of the substantially cylindrical lateral surface of the base,
    and wherein step d) includes causing all the radial receiving lugs to enter the respective engagement interfaces by a simple combined movement of translation.

6. The method of claim 5, further comprising the step of affixing the free ends of the petals, by welding or adhesive bonding, to a substantially cylindrical lateral surface of the base.

7. The method of claim 6, further comprising providing the free end of each petal with at least one engagement interface having a notch which is formed in the end edge of the petal and in which one of the radial receiving lugs of the base engages.

8. The method of claim 7, further comprising providing each petal with two lateral edges extending radially from the central zone as far as the end edge, and providing each petal with an engagement interface having two substantially L-shaped notches, respectively, formed between the end edge and one of the lateral edges.

9. The method of claim 8, further comprising forming the branches in the shape of a cross.

\* \* \* \* \*